United States Patent [19]

Roseiro

[11] Patent Number: 4,826,432
[45] Date of Patent: May 2, 1989

[54] DENTAL APPARATUS FOR ODONTOPEDIATRICS

[76] Inventor: Antonio H. R. Roseiro, 29,Lazarim, 2825 Monte Da Caparica, Portugal

[21] Appl. No.: 70,547

[22] Filed: Jul. 7, 1987

[30] Foreign Application Priority Data

Sep. 8, 1986 [PT] Portugal .................................. 83329

[51] Int. Cl.⁴ .............................................. A61G 1/14
[52] U.S. Cl. ......................................... 433/79; 433/77
[58] Field of Search ............................ 433/77, 78, 79; 446/279, 289, 290, 297

[56] References Cited

U.S. PATENT DOCUMENTS

| | | | |
|---|---|---|---|
| 2,138,563 | 11/1938 | Voorhees | 433/78 |
| 2,308,812 | 1/1943 | Jankelson | 433/77 |
| 2,351,943 | 6/1944 | Ebbers et al. | 433/77 |
| 2,881,559 | 4/1959 | Glass | 446/289 |
| 3,210,846 | 10/1965 | Balkin | 433/79 |
| 3,949,480 | 4/1976 | Page | 433/78 |
| 4,307,891 | 12/1981 | Doornick et al. | 446/290 |

Primary Examiner—John J. Wilson
Attorney, Agent, or Firm—Lackenbach Siegel Marzullo & Aronson

[57] ABSTRACT

The invention consists of an apparatus for odontopediatrics, characterized by a prop in the shape of a humanoid Robot(1), transported on four wheels(2) activated by a radio-controlled electric motor in which various accessories for odontologic treatments have been installed, as well as diverse ludicous equipment for entertaining and attracting the attention of young patients.

11 Claims, 10 Drawing Sheets

DENTAL APPARATUS FOR ODONTOPEDIATRICS

THE SCOPE OF THE INVENTION

The present invention has to do with a dental apparatus for odontopediatrics.

A GENERAL DESCRIPTION OF THE INVENTION

One of the existing problems with which odontopediatrics have to contend resides in the fact that the usual equipment found in the dentists consulting romm, the instruments employed by him and/or the general atmosphere in the consulting room, all go to create a sense of fear and anguish in the child requiring treatment, thus hindering the treatment and the success of the professional Doctor and his respective assistants.

The present invention is a dental apparatus for odontopediatrics whose principal object is that of resolving the referred problem, in a satisfactory manner.

This dental apparatus permits us to show the children all the odontologic instruments required for the various treatments, in an attractive way, as well as its exterior aspect which attracts the attention of the child requiring treatment it also contains a set of ludicous gadgets which we shall describe in detail further on, and are destined to desviate the child's attention during and after treatment. This has been put into practice and gave positive results.

According to the present invention the exterior of the apparatus looks like a humanoid robot that moves on castors operated by electricity and is painted in bright colours, to draw the children's attention.

A BRIEF DESCRIPTION OF THE DRAWINGS

In the annexed designs we represent a preferred form of the present invention of which follows a description to exemplify, not to limit.

Therefore.

DESCRIPTION OF A PREFERRED FORM OF REALIZATION

As is explained clearly in FIGS. 1 to 5, the dental apparatus, according to the present invention, is designated generically by (1) having the aspect of a humanoid robot divided in three fundamental parts:

Head (25),

Trunk (14) with its upper members bent, approximately at an angle, and the Base (20) resting on wheels of which six are free and wild, and two (2) that are activated by an electric motor.

The aspect on the outside of the robot immediately attracts the attention of children undergoing treatment, this is intensified by the colours used for the electric bulbs of nose and eyes. The colours employed in painting the outside also being suitable for young children.

In accordance with this preferred form of executing the present invention you will find the following ludicous equipment installed in the robot.

1. a green transparent helmet (3) with an anti-collision system transports for emergencies.

2. an electric bulb is a nose which can be lit up by the regularity of the movement of the psychedelic unit or by constant frequency. This can also be used alternately.

3. two small electric bulbs set into the eyes light up in the same way as the nose. These actions can also act independently or simultaneously.

4. a cassette recorder of which the electronic module is kept in a packet in the form of a parallelepiped box (19) is installed on the back of the robot, and has outlets leading to loudspeakers installed, preferably, in the mouth of the robot and/or to auriculars which may be put in the ears of the child undergoing treatment and if wished, reproduce the sounds recorded on the cassette, with the option of introducing a deformation of the sounds in order to give then the metallic timbre associated with robot speech.

And still for use in this medical unit a transmitor/-receiver of voice signals modulated on F.H. with an infra-red carrier, picked up and emitted by aerial (27) where a pre-contact can be established between doctor/patient, the latter being unaware of the former in the first visual contacts.

The antenna (27) is circular and is found beneath the green helmet already mentioned in paragraph 1. It also serves for the reception of codefied signals in the remote control of the traction motors of the unit. In this emission the carrier is also infra-red.

In the reception of sound, via communications by infra-red waves, it goes through "delay" of sound where it is transformed and then finally presented as a humanoid voice.

All sounds proceeding from communication, local microphone and deck-cassette as well as passing through "delay" of sound, can also command the psychadelic unit by showing the effects of light on the eyes and nose of the unit.

On the other hand, and is clearly shown in FIGS. 1 to 5, in this preferred form of the present invention, it is foreseen that the following gadgets for odontologic treatment will be conveniently installed.

(a) a slow rotating micromotor (11) with its respective accessories and a control servicevalve for odontologists is mounted on a special rest in one of the robots hands (10);

(b) a fast rotating turbine with respective accessories and a control valve for odontologic treatment is mounted on a special rest, in one of the robots hands (12);

(c) a syringe for air or water (15) is suspended from a hook in the lower centre of the robot's chest;

(d) a negascope (16) for the observations of X-ray plates is installed in the upper centre of the robot's chest (14).

1.—On the other hand alongside, the edge of the upper part of the robot's chest (14) and around its circumference, we find various bulbs installed, these (18) tell us how the various odontologic accessories and each of the ludicous gadgets, is behaving. There are also several electric switches and commutators (17) which permit the control or changing of the conditions in which the gadgets are functioning.

2.—In the preferred form of the robot for this present invention the supply of electric energy, compressed air and water for the various individual gadgets installed in the robot is done respectively through a distribution system of electric energy where it will be stored in batteries for future use. The same occurs in the distribution of compressed air and water properly installed in the interior of the robot, with the appropriate control knobs and commutators mounted on the chest of the robot, and are the only accessible parts in sight of the respective system. Each system is connected to its proper outside source by means of a rapid system of connection (21) in the posterior of the base of the robot (20).

In order that the distribution of the pressure of the compressed air can be properly controlled, there is a manually controlled valve, in the anterior part of the base of the robot (20). This enables compressed air to be distributed to the respective odontologic accessories, there is also a manometer (23). This indicates the respective valve of the pressure.

A pedal (26) with an electric micro-switch incorporated, allows the dentist to switch on or off, the supply of electric current as required, leaving both of the dentists hands free, therefore available for any necessary for odontologic treatments.

The furnishing of water and compressed air to each of the odontologic accessories is interrupted or established by means of a service valve, individually controlled, by a lever installed beside each accessory.

In turn the feeding system for fluids to each of the mentioned odontologic gadgets (a), (b), (c) terminate beside the gadget by means of pieces of hose rolled spirally (24) of the type usually employed for this effect in odontologic apparatus already known in the actual technique.

On the robot's back, coming from one of the lateral sides of the parallelepipedal box where the deck cassette is to be found (19) an aerial is installed (6) which, besides being decorative, can also be used as a reception antenna for radio signals such as, in the case of when the electric motor which moves the wheels is being controlled by radio.

In accordance with the present invention, the base for the odontopediatric equipment sits on eight wheels (2) these wheels permit it to move freely along the consulting room floor whenever it is required. The electric motors that move the wheels are found in the interior of the base (20). To control the wheels there is a switch, adequately fitted in the inside edge of the robots chest (14). There is also an inversor.

In FIGS. 6 to 10 you will find schematically represented, the various circuits for the supply of electric energy, compressed air and water to the most important component parts of the dental unit, in accordance with the present invention.

A simple observation is practically all that is needed for a fuller understanding of how the unit works. A descriptive passage of each of the figures is also included.

Figure 6:
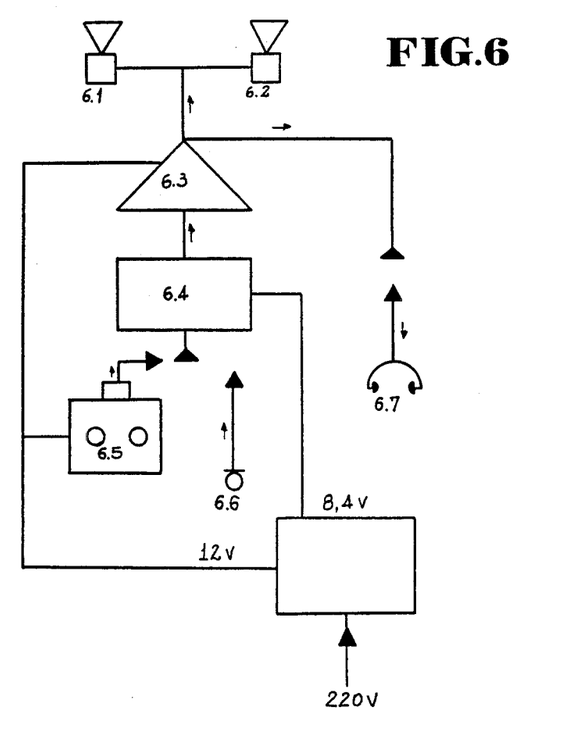
FIGS. 6 and 7 respectively, shows a scheme of the electric circuits for the electronic equipment and for the supply of electricity used for the apparatus on castors.

Therefore, the reference numbers and arrows that exist in FIG. 6, correspond with the following components:

6.1. and 6.2.—loudspeakers;
6.3.—linear amplifier;
6.4.—"Delay" line
6.5.—cassette deck;
6.6.—microphone;
6.7.—auriculars and sound.

Figure 7:
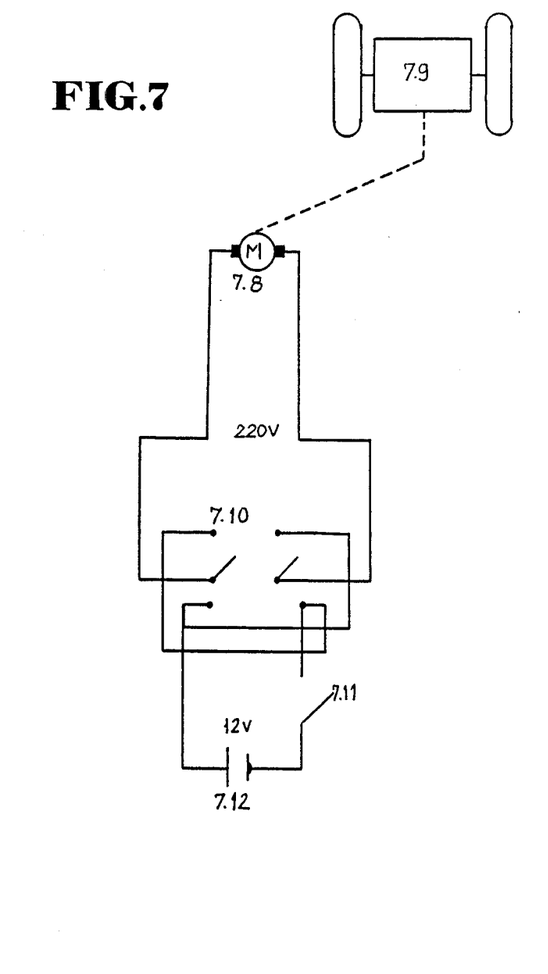

In turn, the reference numbers which appear in FIG. 7, correspond with the following components:

7.8.—traction electric motor;
7.9.—wheel system;
7.10.—inversor;
7.11.—switch;
7.12.—battery.

Figure 8:
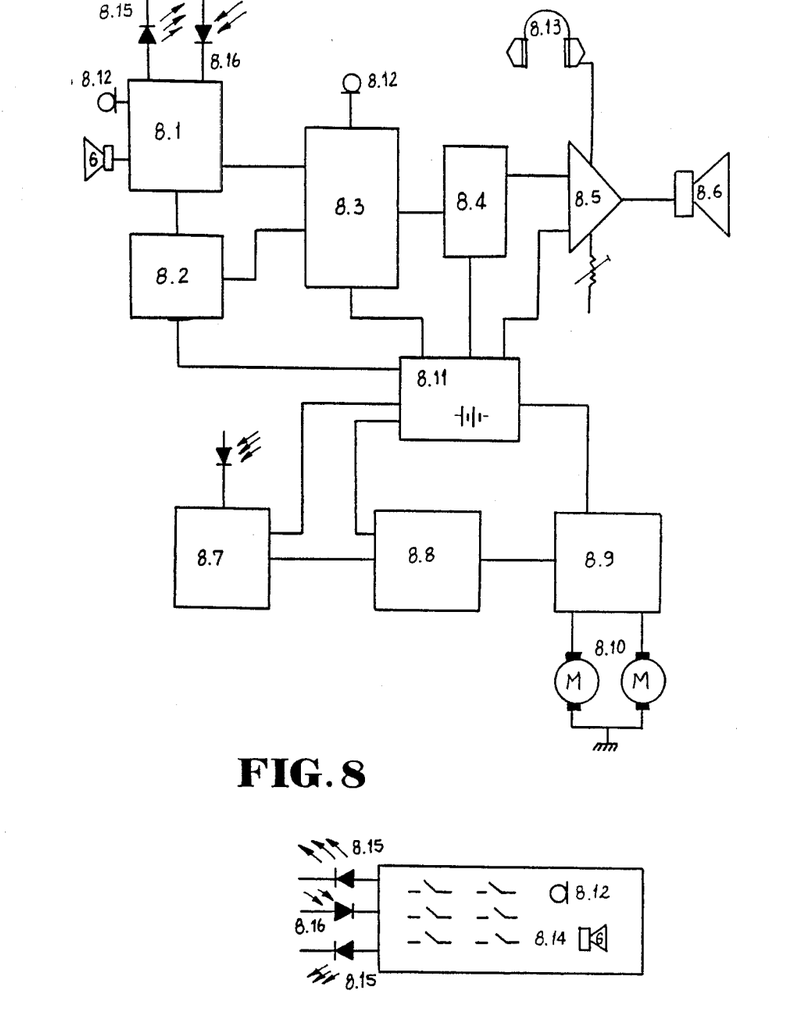
FIG. 8 represents schematically, in the form of a diagram of blocks, the electric circuit for the control of the wheels by means of infra red radiation, as well as distant control.

The reference numbers used in FIG. 8, correspond with the following components:

8.1.—infrared transmitter and receiver;
8.2.—cassette deck;
8.3.—audio mixer;
8.4.—"delay";
8.5.—operational amplifier;
8.6.—loudspeaker;
8.7.—infra-red receiver;
8.8.—information decodifier;
8.9.—service command;
8.10.—motors;
8.11.—battery;
8.12.—microfone;
8.13.—earphones;
8.14.—distant control;
8.15.—"led" infra-red transmitter;
8.16.—"led" infra-red receiver.

Figure 9:
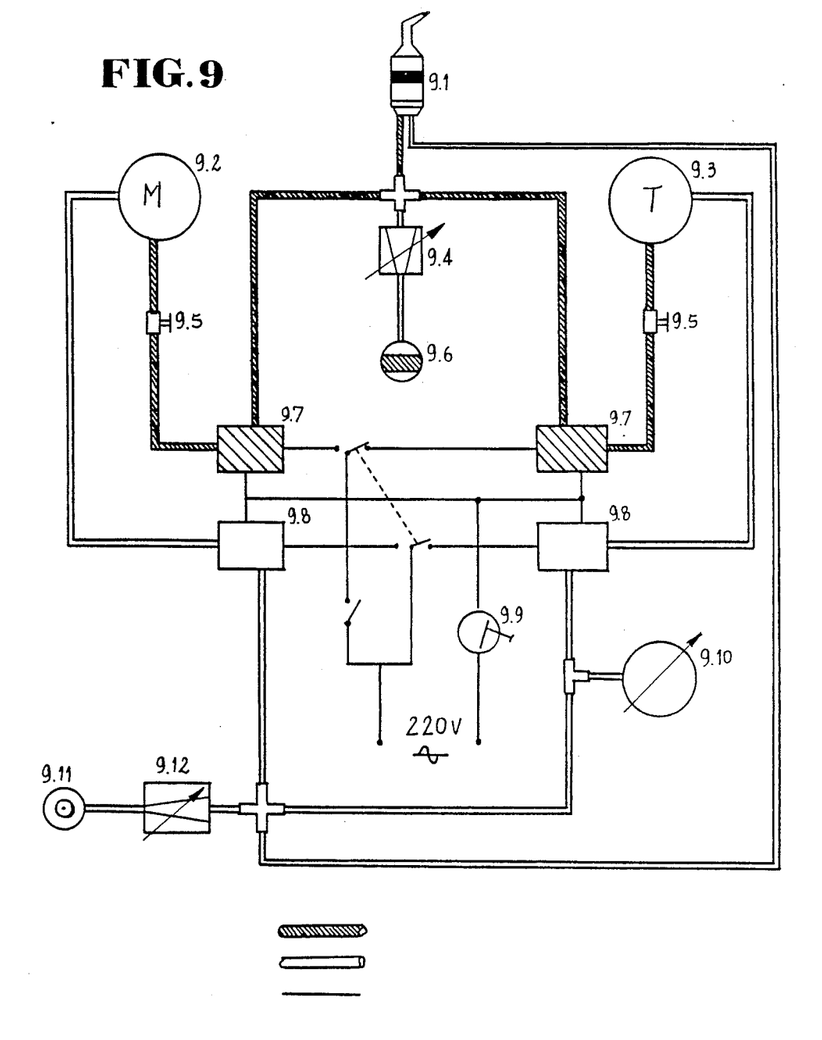
FIG. 9 represents schematically a diagram of the circuits for the distribution of electricity, water and air which have been established in the robot in accordance with the present invention.

As regards, FIG. 9, the following components correspond with the numbers indicated below:

9.1.—syringe;
9.2.—micromotor;
9.3.—turbine;
9.4.—water regulator;
9.5.—tap;
9.6.—water socket;
9.7.—electrovalve for water;
9.8.—electrovalve for air;
9.9.—pedal;
9.10.—manometer;
9.11.—air socket
9.12.—regulator.

Figure 10:
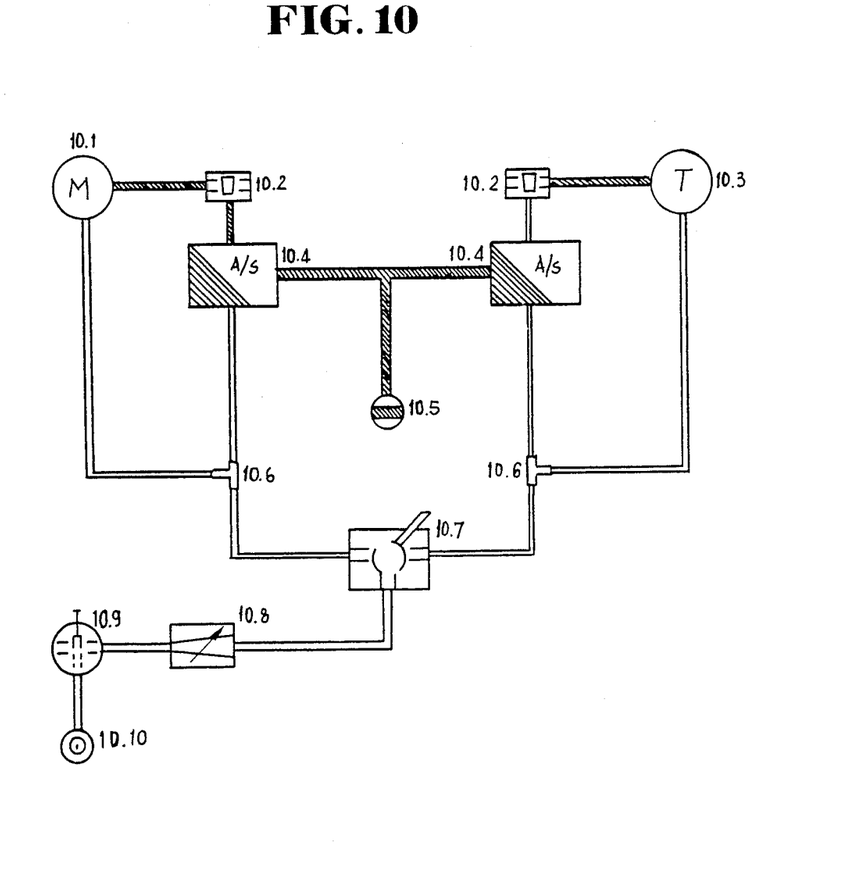
FIG. 10 represents schematically, the system used for feeding water/air to the odontologic accessories of the dental apparatus in accordance with the present invention.

Finally, the reference numbers used in FIG. 10 correspond with the following components of the odontologic apparatus, in accordance with the present invention:

10.1.—micromotor;
10.2.—water tap;
10.3.—turbine;
10.4.—automatic for sprays;
10.5.—water socket;
10.6.—T shaped passage;
10.7.—water inversor;
10.8.—air regulator;
10.9.—pedal;
10.10.—air socket.

Constituting improvements, in relation to the form of the present descriptive invention, it is possible to fashion the functioning of the electric motor that moves the wheels, so that it may be controlled by radio (in this case the antenna (6) is able to capture and reinforce radio signals for the control of operations) or to be controlled by means of infra-red rays (see circular antenna 27).

In the preferred form of the present invention which has just been described, exemplifying, and in no way limited, numerous alterations and changes can be introduced which obviously may be embodied in the ambit of the invention.

Figure 1:
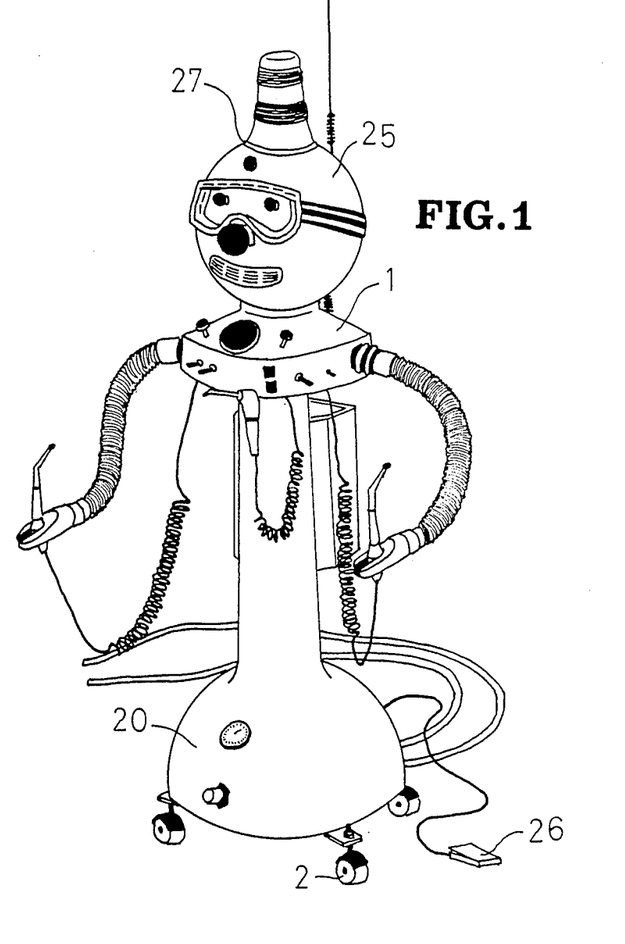
FIG. 1, represents the preferred form of realizations, in perspective.
Figure 2:
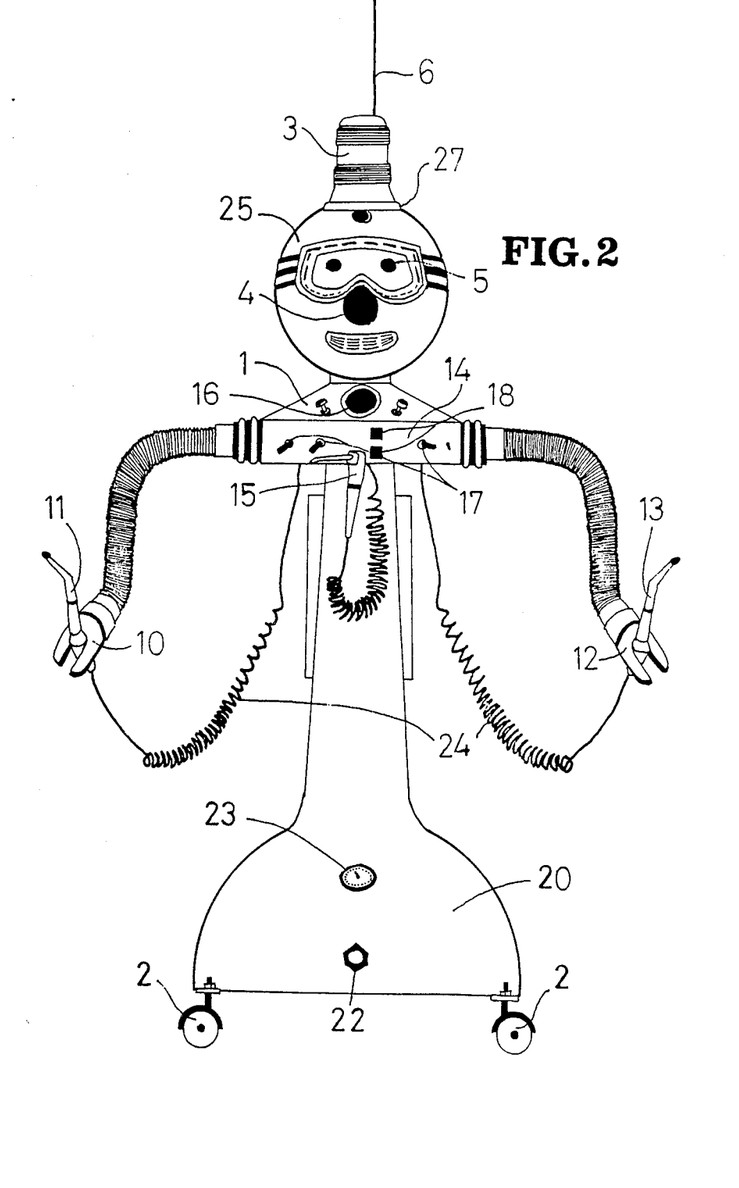
FIG. 2, shows us an upright front view.
Figure 3:
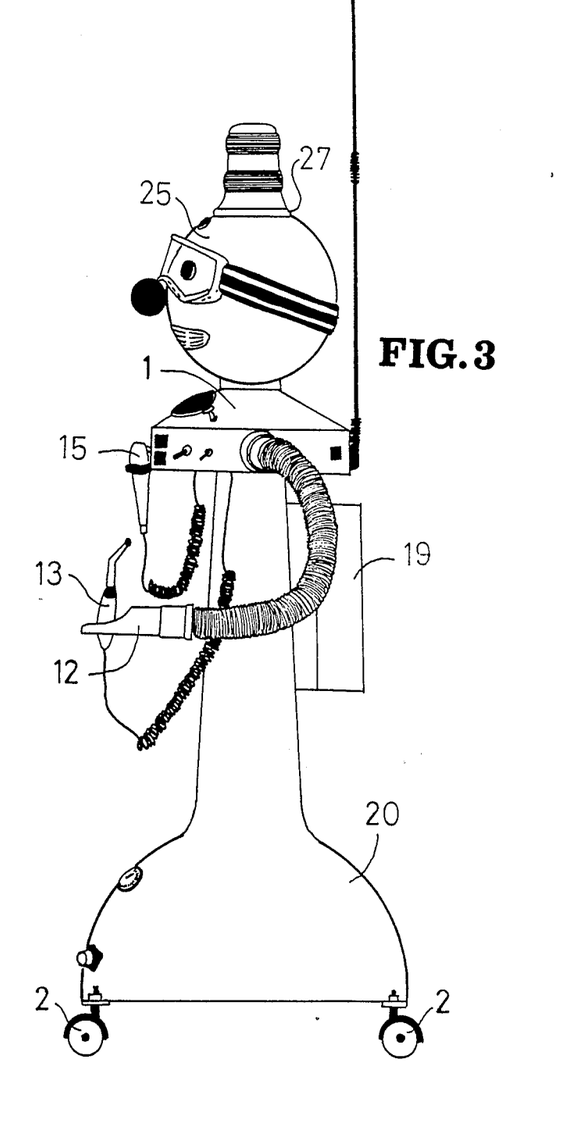
FIG. 3, an upright lateral view from the left.
Figure 4:
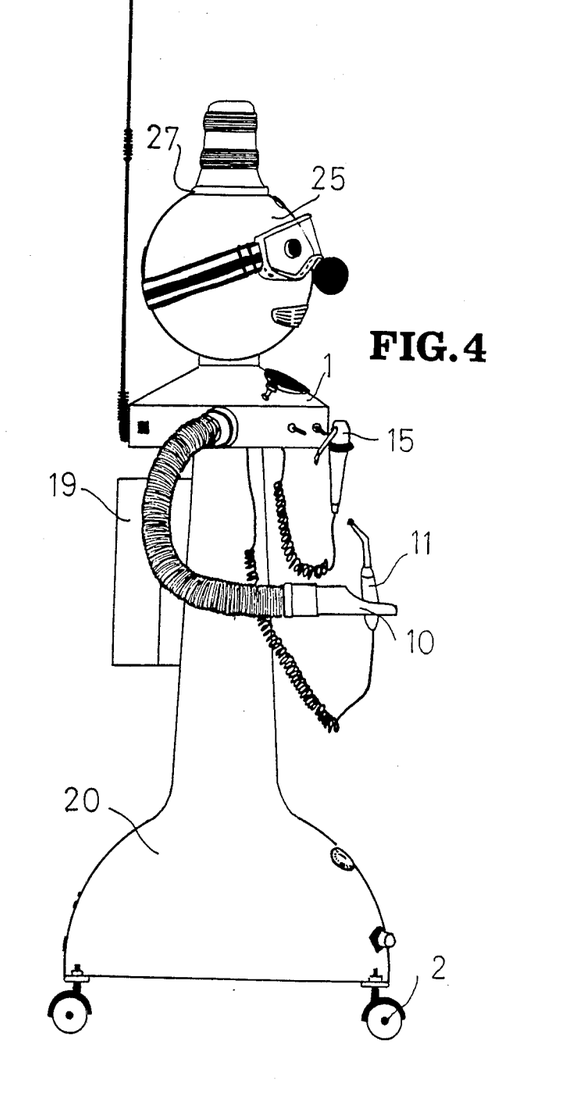
FIG. 4, an upright lateral view from the right.
Figure 5:
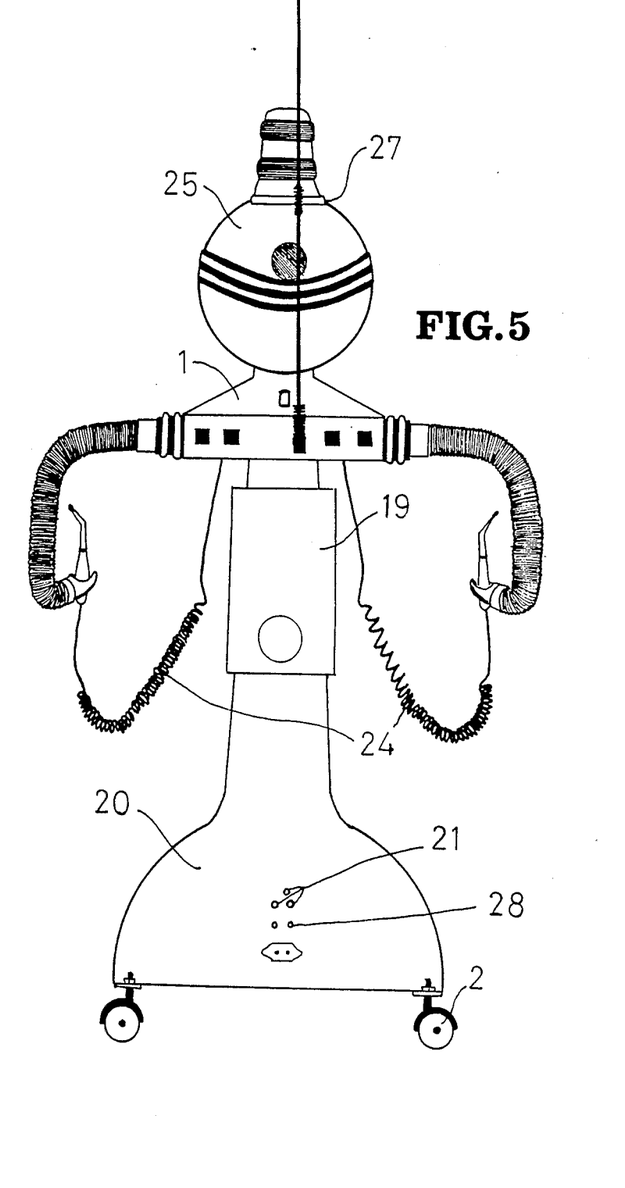
FIG. 5, an upright posterior view.

Therefore, we foresee:

(a) the hose, rolled spirally, that feeds the fluids (water and compressed air) to the diverse odontologic accessories during their functioning, as FIGS. 1 and 2 demonstrate come from the inside edge at the front of the robot's chest (14) in the finished form described they will be gathered inside the robot's arms and come out near its hands.

(b) the robot's arms will be articulated therefore, the hands that hold the odontologic accessories can assume various positions in space depending on the doctor's wishes.

(c) the robot's head is able to turn both right and left.

(d) as another additional odontologic accessory there will be an ultrasonic system for the elimination of tartar.

(e) there will also be a system of cold light for the polymerization of composites.

(f) a system of fiber optics for the observation of mouth cavities will also be installed.

(g) a microprocessor will also be installed for remote control or functions which have been omitted here.

According to the present invention the functioning of the odontopediatric apparatus is exactly similar to that is being done at present. The function of the ludicous is obvious.

The fact of having the appearance of a humanoid robot and possessing a set of various ludicous accessories, adequately chosen to attract the child's attention, by entertaining the child before and after treatment, simplifies the work of the doctor and his assistants work thus avoiding the disagreeable consequences of fright in most children when submitted to dental treatment.

Any specialist on this subject may introduce other alterations and/or modifications in the form or forms of the realization of the dental appliance for odontopediatrics, in accordance with the present invention, in this we expect that the spirit or the objectives of the present invention will not be removed, this also refers to the ambit as it is described in reclamations this should be considered included in the ambit.

I claim:

1. Dental apparatus for odontopediatrics, characterized in that, on a support in the form of a humanoid robot, which can be moved on four wheels, said support including two elongated projections corresponding to right and left arms, special supports corresponding to right and left hands at the ends of said arms and an area between the projections corresponding to the chest of the robot, (a) on said special support corresponding to the respective right hand, a slowly rotating micromotor and corresponding accessories for odontological treatment;

(b) on said special support for the respective left hand, a rapidly rotating turbine and corresponding accessories for odontological treatment;

(c) on the central front part of the vertical edge of the chest of the robot and suspended on a hook, an air or water syringe;

(d) on the central inclined part of the chest of the robot, a negatoscope for inspection of X-ray plates;

(e) arranged on the periphery of the vertical edge of the chest of the robot, several control switches and commutators and bulbs to indicate the condition of operation of the diverse accessories and also the play functions of the robot;

(f) in a shaped box, imitating a bag carried on the back of the robot, a completely enclosed cassette recorder-player;

(g) on the rear part of the base of the robot, connections of the rapid type for supplying electric current, water and compressed air to the diverse accessories of the apparatus and electrical connection to a pedal with microswitch for activation with the foot;

(h) on the front part of the base of the robot, valve for control of the pressure of the air and manometer distributed to the accessories; and (i) systems for distributing electric current, water and air suitably mounted in the hollow interior of the robot to supply the diverse accessories.

2. Dental apparatus for odontopediatrics according to claim 1, characterized in that it also comprises an ultrasound system for removing tartar.

3. Dental apparatus for odontopediatrics according to claim 1, characterized in that it also comprises a cold light system for polymerization of composites.

4. Dental apparatus for odontopediatrics according to claim 1, characterized in that it comprises a fibre-optics system for buccal inspection.

5. Dental apparatus for odontopediatrics according to claim 1, characterized in that the supply of the fluids to the accessories (a) (b) and (c) is achieved by means of conventional spirally wound hoses.

6. Dental apparatus for odontopediatrics according to claim 5, characterized in that the hoses supplying fluid to the accessories (a) and (b) are contained inside the arms of the robot.

7. Dental apparatus for odontopediatrics according to claim 1, characterized in that the arms of the robot are articulated.

8. Dental apparatus for odontopediatrics according to claim 1, characterized in that the movement of the robot is achieved by means of activation by an electric motor installed in its base which acts on a wheel.

9. Dental apparatus for odontopediatrics according to claim 8, characterized in that the operation of the electric motor is radio-controlled.

10. Dental apparatus for odontopediatrics according to claim 1, characterized in that the head of the robot can have a horizontal rotating movement from one side to the other.

11. Dental apparatus for odontopediatrics according to claim 1, characterized in that it has one or more headphones and microphones connected to the cassette recorder-player enclosed in the box, allowing the recording and the reproduction of the voice with or without distortion.

* * * * *